United States Patent [19]

Allison et al.

[11] Patent Number: 4,992,467
[45] Date of Patent: Feb. 12, 1991

[54] TREATMENT OF AUTOIMMUNE DISEASES WITH MYCOPHENOLIC ACID, AND DERIVATIVES AND FORMULATIONS THEREOF

[75] Inventors: Anthony C. Allison; Elsie M. Eugui, both of Belmont; Peter H. Nelson, Los Altos; Chee-Liang L. Gu, Sunnyvale; William A. Lee, Palo Alto, all of Calif.

[73] Assignee: Syntex (U.S.A.) Inc., Palo Alto, Calif.

[21] Appl. No.: 500,439

[22] Filed: Mar. 28, 1990

Related U.S. Application Data

[60] Division of Ser. No. 373,413, Jun. 29, 1989, Pat. No. 4,948,793, which is a division of Ser. No. 233,200, Aug. 17, 1988, Pat. No. 4,868,153, which is a division of Ser. No. 146,883, Jan. 22, 1988, Pat. No. 4,786,637, which is a continuation-in-part of Ser. No. 8,717, Jan. 30, 1987, Pat. No. 4,753,935, said Ser. No. 373,413, is a division of Ser. No. 272,161, Nov. 14, 1988, which is a division of Ser. No. 93,459, Sep. 4, 1987, Pat. No. 4,808,592, which is a division of Ser. No. 8,717.

[51] Int. Cl.$^5$ .............................................. A61K 31/36
[52] U.S. Cl. .................................................. 514/464
[58] Field of Search ......................................... 514/464

[56] References Cited

U.S. PATENT DOCUMENTS

| | | | |
|---|---|---|---|
| 3,705,894 | 6/1972 | Gerzon et al. | 260/240 R |
| 3,777,020 | 7/1973 | Johnson | 424/180 |
| 3,825,571 | 4/1974 | Mori et al. | 260/343.3 |
| 3,853,919 | 5/1974 | Mori et al. | 260/343.3 |
| 3,868,454 | 5/1975 | Johnson | 424/248 |
| 3,880,995 | 6/1975 | Jones | 424/180 |
| 3,903,071 | 7/1975 | Holmes | 260/210 R |

FOREIGN PATENT DOCUMENTS

| | | |
|---|---|---|
| 48-86860 | 6/1973 | Japan. |
| 48-86861 | 6/1973 | Japan. |
| 57-024380 | 3/1982 | Japan. |
| 57-183776 | 9/1982 | Japan. |
| 57-183777 | 9/1982 | Japan. |
| 1157100 | 12/1969 | United Kingdom. |
| 1261060 | 6/1972 | United Kingdom. |
| 2117238 | 9/1983 | United Kingdom. |

OTHER PUBLICATIONS

"Antitumor Activity of Derivatives of Mycophenolic Acid", Suzuki, et al., J. Antibiotics, 29(3), 275-285, 1975.

"Carbamoyl Mycophenolic Acid Ethylester, An Oral Antitumor Agent", Suzuki, et al., J. Antibiotics, 29(3), 286-291, 1975.

"Antitumor and Immunosuppressive Effects of Mycophenolic Acid", Ohsugi, et al., Cancer Research, 36, 2923-2927, 1976.

"A Gastroprotective Anti-Inflammatory Agent: The β-morpholinoethyl Ester of Niflumic Acid (Morniflumate)", Schiantarelli, et al., Agents and Actions, 14(2), 1984.

Primary Examiner—Stanley J. Friedman
Attorney, Agent, or Firm—David A. Lowin; Tom M. Moran

[57] ABSTRACT

The compounds and pharmaceutical compositions of Formula A, wherein Z is hydrogen or —C(O)R, Y is hydrogen or morpholinoethyl, and where R is lower alkyl or aryl, and the pharmaceutically acceptable salts thereof, are useful as immunosuppressive agents, particularly for treatment of allograft rejection, especially including cardiac allograft rejection, pancreatic allograft rejection and renal allograft rejection, and for treating autoimmune diabetes.

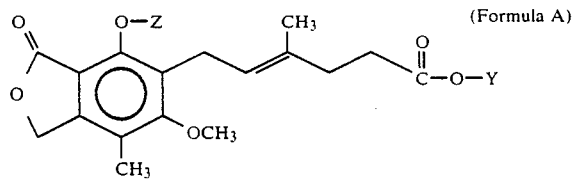

6 Claims, No Drawings

TREATMENT OF AUTOIMMUNE DISEASES WITH MYCOPHENOLIC ACID, AND DERIVATIVES AND FORMULATIONS THEREOF

CROSS-REFERENCE TO RELATED APPLICATIONS

This is a division of pending application Ser. No. 373,413, filed June 29, 1989, U.S. Pat. No. 4,948,793; which in turn is a division of Ser. No. 233,200, filed Aug. 17, 1988, now U.S. Pat. No. 4,868,153; which is a division of Ser. No. 146,883, filed Jan. 22, 1988, now U.S. Pat. No. 4,786,637; which is a continuation-in-part of Ser. No. 008,717, filed Jan. 30, 1987, now U.S. Pat. No. 4,753,935, all incorporated herein by reference. Ser. No. 373,413 is also a division of application Ser. No. 272,161, filed Nov. 14, 1988, filed Sept. 4, 1987, now U.S. Pat. No. 4,808,592; which is a division of Ser. No. 008,717, filed Jan. 30, 1987, now U.S. Pat. No. 4,753,935, all incorporated herein by reference.

BACKGROUND OF THE INVENTION

1. Field of the Invention

The present invention relates to methods of treatment, especially for treating allograft rejection, with pharmaceutical compositions, particularly with mycophenolic acid, the morpholinoethyl ester thereof and certain simple ester derivatives of the phenolic hydroxyl group. Methods of treatment for autoimmune diseases, such as diabetes are also disclosed.

2. Background Information and Related Disclosures

Inflammatory diseases, in particular rheumatoid arthritis, have been treated with a variety of compounds repressing several structural classes and biological activities, including, for example, anti-inflammatory agents (corticosteroids, aspirin, derivatives of arylacetic and arylpropionic acids, and oxicams), immunosuppressive agents and regimens (methotrexate, cyclophosphamide, cyclosporin, and total lymphoid irradiation), and long-acting anti-rheumatic drugs (gold salts, and penicillamine and its derivatives). However, no representative of any of these classes of compounds is regarded as ideal.

Mycophenolic acid is a weakly-active antibiotic found in the fermentation broth of *Penicillium brevicompactum*. Some compounds relating to mycophenolic acid, and their uses in the treatment of inflammatory diseases, such as rheumatoid arthritis, are disclosed in the following two prior related applications.

Ser. No. 803,041, filed Nov. 27, 1985, relates to compounds having the general structure of Formula 1:

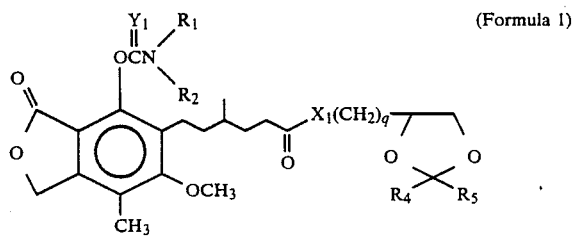

(Formula 1)

and the pharmaceutically acceptable salts thereof, where:

$R_1$ is H or lower alkyl having 1 to 6 carbon atoms;
$R_2$ is H, lower alkyl having 1 to 6 carbon atoms or -phenyl-4-$CO_2R_3$, in which $R_3$ is H, lower alkyl having 1 to 6 carbon atoms or a pharmaceutically acceptable cation;
$R_4$ and $R_5$ are each independently H or lower alkyl having 1 to 6 carbon atoms;
$X_1$ and $Y_1$ are each independently O or S; and
q is an integer of 1-6.

Ser. No. 821,633, filed Jan. 23, 1986, relates to compounds having the general structure of Formula 2:

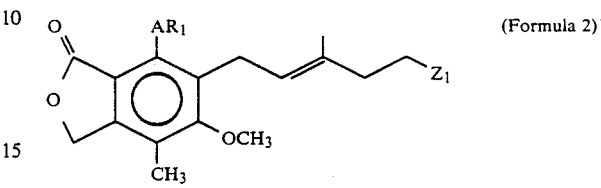

(Formula 2)

and the pharmaceutically acceptable salts thereof, where:

A is oxygen or sulfur;
$R_1$ is selected from the group consisting of:

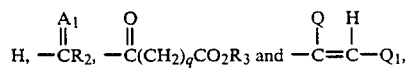

in which:

$A_1$ is oxygen or sulfur;
q is an integer form 0-6;
$R_2$ is alkyl, haloalkyl or $-NR_4R_5$, where: $R_4$ and $R_5$ are independently H, alkyl, haloalkyl, cycloalkyl, phenyl optionally monosubstituted with halogen, hydroxy, carboxy, chlorocarbonyl, sulfonylamino, nitro, cyano, phenyl, alkyl, acyl, alkoxycarbonyl, acylamino, dialkylamino or dialkylaminoethoxycarbonyl, phenyl optionally disubstituted with hydroxy, carboxy, notro or alkyl, or benzyl optionally substituted with dialkylamino;
$R_3$ is H, alkyl or a pharmaceutically acceptable cation;
Q and $Q_1$ are independently H or $-CO_2R_3$; and
$Z_1$ is selected from the group consisting of: IH-tetrazolyl, $-CH_2OH$, $-CHO$, $-CN$, $-C(O)A_2R_6$ and $-C(O)NR_7R_8$, in which:
$A_2$ is oxygen or sulfur;
$R_6$ is H, alkyl, alkenyl, cycloalkyl, optionally substituted phenyl, optionally substituted benzyl or a pharmaceutically acceptable cation; and
$R_7$ and $R_8$ are independently H, alkyl or cycloalkyl, or $R_7$ and $R_8$ taken together are $-(CH_2)_2O(CH_2)_2-$, $-(CH_2)_4-$,m or $-(CH_2)_5-$;
with the proviso that $R_1$ and $R_6$ cannot both be H if A and $A_2$ are oxygen.

Compounds somewhat structurally similar to the compounds of Formulae 1 and 2 are described in U.S. Pat. Nos. 3,705,894; 3,853,919; 3,868,454; 3,880,995, in Japanese Patent No. J 57024380, in *J. Antibiot.*, 293), 275-85, 286-91 (1976), and in *Cancer Research*, 368), 2923-7 (1976). The disclosed compounds are described as having anti-tumor, immunosuppressive, anti-viral, anti-arthritic and/or anti-psoriatic activities.

SUMMARY OF THE INVENTION

One aspect of the present invention concerns methods for treating allograft rejection, especially including cardiac allograft rejection, pancreatic allograft rejection and renal allograft rejection, and for treating autoimmune diseases including diabetes, by administering to an animal in need thereof an effective amount of mycophenolic acid, the morpholinoethyl ester of ycophenolic acid and certain derivatives thereof mycophenolic acid, i.e., compounds having the structure of Formula A, which follows:

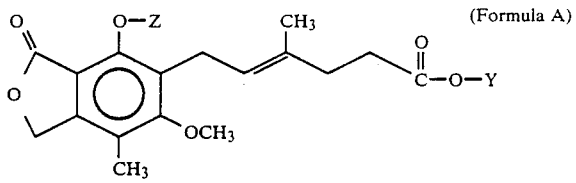

wherein:
Y is morpholinoethyl (i.e.,

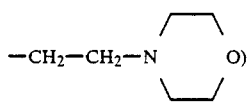

or hydrogen, and
Z is hydrogen or —C(O)R,
where R is lower alkyl and aryl,
and the pharmaceutically acceptable salts thereof.

In another aspect, the invention relates to a pharmaceutical composition for effecting such treatment, containing a therapeutically effective amount of a compound of Formula A admixed with at least one pharmaceutically acceptable excipient.

DETAILED DESCRIPTION OF THE INVENTION

Definitions and General Parameters

The following definitions are set forth to illustrate and define the meaning and scope of the various terms used to describe the invention herein.

The numbering of the mycophenolic acid is as follows:

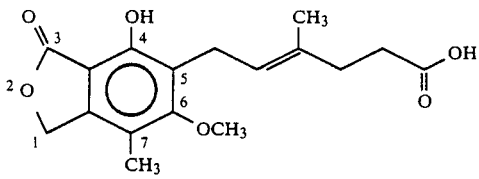

The compounds of the invention will be named using the above-shown numbering system as the morpholinoethyl esters of E-6-(1,3-dihydro-4-hydroxy-6-methoxy-7-methyl-3oxo-5isobenzofuranyl)-4-methyl-4-hexenoic acid and its derivatives. The compounds of the present invention are prepared as the E (or Entgegen) position isomer. Some representative compounds are named as follows:
the compound of Formula A where Z is —C(O)R, Y is morpholinoethyl, and wherein R is methyl is named "morpholinoethyl E-6-(1,3-dihydro-4-acetoxy-6-7-methyl-3-oxo-5-isobenzofuranyl)-4-methyl-4-hexenoate" and
the compound of Formula A where Z is —C(O)R, Y is morpholinoethyl, and where R is phenyl is named "morpholinoethyl E-6-(1,3-dihydro-4-benzoyloxy-6-methoxy-7-methyl-3-oxo-5-isobenzofuranyl)-4-methyl-4-hexenoate".

As used herein, the term "alkyl" refers to a fully saturated monovalent radical containing only carbon and hydrogen, and which may be a cyclic, branched or straight chain radical. This term is further exemplified by radicals such as methyl, ethyl, t-butyl, pentyl, heptyl and pivalyl.

The term "lower alkyl" refers to a monovalent alkyl radical of one to six carbon atoms. This term is further exemplified by such radicals as methyl, ethyl, n-propyl, isopropyl, n-butyl, t-butyl, i-butyl (or 2-methylpropyl), isoamyl, pentyl, and isopentyl.

The term "aryl" refers to a substituted or unsubstituted monovalent unsaturated aromatic carbocyclic radical having a single ring (e.g., phenyl) or two condensed rings (e.g., naphthyl).

The term "acyl" refers to a radical based on an organic acid, e.g., —C(O)R$^1$ where F$^1$ is alkyl or aryl.

As used herein, the term "halo" refers to fluoro, bromo, chloro and iodo.

Isolation and purification of the compounds and intermediates described herein can be effected, if desired, by any suitable separation or purification procedure such as, for example, filtration, extraction, crystallization, column chromatorgraphy, thin-layer chromatography or thick-layer chromatography, or a combination of these procedures. Specific illustrations of suitable separation and isolation procedures can be found by reference to the examples hereinbelow. However, other equivalent separation or isolation procedures can, of course, also be used.

A "pharmaceutically acceptable salt" may be any salt derived from an inorganic or organic acid. The term "pharmaceutically acceptable anion" refers to the anion of such salts. The salt and the anion are chosen not to be biologically or otherwise undesirable. These salts are formed with inorganic acids such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluensulfonic acid, salicylic acid and the like.

As used herein, the term "treatment" or "treating" means any treatment of a disease in a mammal, and includes:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

Unless specified to the contrary, the reactions described herein take place at atmospheric pressure over a temperature range from about 10° C. to about 100° C., more preferably from about 10° C. to about 50° C., and most preferably at about room temperature.

Preparation of the Compounds of Formula A

The compounds of Formula A can be prepared according to several synthetic pathways, depending upon the substitution at Z, typically starting with mycophenolic acid, which is commercially available. Where Z is —C(O)R, the phenolic oxygen of mycrophenolic acid can be acylated either before or after the esterification of the acid. Where Z is hydrogen, the starting material is typically mycophenolic acid.

Morpholinoethyl Esterification of Mycophenolic Acids

Many standard esterification procedures may be used, for example, as described in *Synthetic Organic Chemistry* by R. B. Wagner and H. D. Zook (Wiley, N.Y.) 1956, see pages 479–532. Two presently preferred synthetic routes are described below for conversion of mycophenolic acid and its derivatives into the morpholinoethyl ester compounds of Formula A. The first route involves conversion into an acid halide, followed by condensation with morpholinoethanol to the end product. The second route involves conversion directly into the end product using a carbodiimide reaction.

As an example, a less preferred third route entails starting with an ester of mycophenolic acid (other than the morpholinoethyl ester) in an ester exchange reaction for conversion into the desired end product.

The Acid Halide-Condensation Route

In the first synthetic route, mycophenolic acid or an acylated derivative thereof is dissolved or suspended in a solvent inert under the conditions of the reaction (i.e., an inert solvent, such as benzene, toluene, acetonitrile, tetrahydrofuran, diethyl ether, chloroform or preferably methylene chloride) and an excess (about 10 molar equivalents to 1) of a halogenating agent (e.g., thionyl chloride) is added, optionally together with a small amount of dimethylformamide. The reaction mixture is stirred for about 1–8 hours, preferably about 4 hours, to yield the corresponding acid halide.

The acid halide is dissolved in an inert solvent, as described above, and reacted by a condensation reaction with a cooled solution (e.g., maintained at about 4° C.) of morpholinoethanol [also named as 4-(2-hydroxyethyl)-morpholine], to which it is added slowly over a period of about 10 minutes to 2 hours, preferably about 90 minutes. The end product of Formula A is isolated and purified by conventional procedures.

The Carbodiimide Route

In the second sythetic route, mycophenolic acid or an acylated derivative thereof is dissolved in a solvent inert under the conditions of the reaction [such as dry tetrahydrofuran ("THF"), dichloromethane, or carbon tetrachloride; preferably THF] and reacted with morpholinoethanol in the presence of a carbodiimide, such as DCC ("dicyclohexylcarbodiimide") or di-p-tolylcarbodiimide. The molar ratio of alcohol to the starting acid is about 1:1. The reaction takes place at atmospheric pressure over a period of about 4–8 hours, preferably over 6 hours. A temperature range from about 10° C. to about reflux temperature, preferably about room temperature may be used. The end product of Formula A is isolated and purified in the usual manner.

Acylation of the Phenolic Oxygen

The compounds of Formula A where Z is —C(O)R are prepared by dissolving mycophenolic acid or the morpholinoethyl ester thereof in an inert organic solvent as defined above (e.g., acetonitrile or preferably pyridine) and reacting it with about 1 to 6 molar equivalents, preferably about 3 molar equivalents, of the appropriate acyl halide or anhydride (e.g., acetic anhydride, propionyl chloride or pivaloyl chloride) in the presence of about 1 to 6 molar equivalents, preferably about 3 molar equivalents, of an inorganic base (such as sodium carbonate, potassium bicarbonate or the like) or a tertiary organic base (such as triethylamine, N-methylpiperidine or preferably pyridine). Certain bases (e.g., pyridine) can also serve as the inert organic solvent. The reaction takes place at a temperature of about 0°–25° C., preferably about 5° C., for about 1–10 hours, preferably about 3 hours. When the reaction is substantially complete, the acylated product is isolated by conventional means.

Salts of Compounds of Formula A

The compounds of Formula A may be converted to corresponding acid addition salts. The conversion is accomplished by treatment with at least a stoichiometric amount of an appropriate acid, such as hydrochloric acid, sulfuric acid, methanesulfonic acid or the like. Typically, the free base is dissolved in a polar organic solvent such as ethanol, methanol, or ethyl acetate and the acid added in water, ethanol, methanol, or isopropanol. The temperature is maintained at 0°–50° C. The resulting salt precipitates spontaneously or may be brought out of solution with a less polar solvent.

A dibasic acid, such as sulfuric acid, can form two salts with the compounds of this invention. One such salt, in which one mole of the base and one mole of the acid are present, is called the fisulfate (or hydrogen sulfate) salt. The other, in which two moles of the base and one mole of the acid are present, is called the sulfate.

The acid addition salts of the compounds of Formula A may be decomposed to the corresponding free bases by treating with an excess of a suitable base, such as ammonia or sodium bicarbonate, typically in the presence of aqueous solvent, and at a temperature of between 0° and 50° C. The free base form is isolated by conventional means, such as extraction with an organic solvent.

Preferred Compounds

Most preferred for use in the methods of treatment of the present invention are the compound of Formula A where Z is hydrogen and Y is morpholinoethyl, i.e., morpholinoethyl E-6-(1,3-dihydro-4-hdryoxy-6-methoxy-7methyl-3-oxo-5-isobenzofuranyl)-4-methyl-4hexenoate, and its pharmaceutically acceptable salts (preferably the hydrochloride, sulfate and bisulfate salts).

Also preferred are the following compounds and pharmaceutically acceptable salts (preferably the hydrochloride, sulfate and bisulfate salts) of Formula A where Z is —C(O)R:
morpholinoethyl E-6-(1,3-dihydro-4-acetoxy-6-methoxy-7-methyl-3oxo-5-isobenzofuranyl)-4methyl-4-hexenoate;
morpholinoethyl E-6-(1,3-dihydro-4-propionyloxy-6-methoxy-7-methyl-3-oxo-5-isobenzofuranyl)-4-methyl-4-hexenoate;
morpholinoethyl E-6-(1,3-dihydro-4-pivaloyloxy-6-methoxy-7-methyl-3-oxo-5-isobenzofuranyl)-4methyl-4-hexenoate; and
morpholinoethyl E-6-(1,3-dihydro-4-benzoyloxy-6-methoxy-7-methyl-3-oxo-5-isobenzofuranyl)-4methyl-4-hexenoate.

Also preferred is mycophenolic acid itself.

Preferred Processes

The compounds used in the present invention can be prepared according to the following last steps:

an E-6-(1,3-dihydro-4-hydroxy-6-methoxy-7-methyl-3-oxo-5-isobenzofuranyl)-4methyl-4hexenoyl haldie, is condensed with morpholinoethanol to give a compound according to Formula A wher Z is hydrogen;

an E-6-(1,3-dihydro-4-hydroxy-6-methoxy-7-methyl-3-oxo-5-isobenzofuranyl)-4-methyl-4-hexenoic acid is contacted with morpholinoethanol in the presence of a carbodiimide to give a compound according to Formula A where Z is hydrogen;

an E-6-(1,3-dihydro-4-acyloxy-6-methoxy-7-methyl-3-oxo-5-isobenzofuranyl)-4-methyl-4-hexenoyl halide, is condensed with morpholinoethanol to give a compound according to Formula A where Z is —C(O)R;

an E-5-(1,3-dihydro-4-acyloxy-6-methoxy-7-methyl-3-oxo-5-isobenzofuranyl)-4-methyl-4-hexenoic acid is condensed with morpholinoethanol in the presence of a carbodiimide to give a compound according to Formula A where Z is —C(O)R;

morpholinoethyl E-6-(1,3-dihydro-4hydroxy-6methoxy-7-methyl-3-oxo-5-isobenzofuranyl)-4-methyl-4hexenoate is condensed with an acyl halide or anhydride to give a compound according to Formula A where Z is —C(O)R;

contacting a pharmaceutically acceptable acid with a compound of Formula A to form the corresponding acid addition salt of Formula A;

substituting a pharmaceutically acceptable acid salt of Formula A with another pharmaceutically acceptable acid; and contacting an acid addition salt of Formula A with a base to form the corresponding free base compounds of Formula A.

Utility and Administration

General Utility

The compounds of Formula A, including the pharmaceutically acceptable salts thereof, and the compositions containing them, are useful in the methods of treatment of the present invention as immunosuppressive agents in mammals, whether domestic (cattle, pigs, sheep, goats, horses), pets (cats, dogs), or preferably humans. They are also useful as anti-inflammatory agents, anti-tumor agents, anti-viral agents, and anti-psoriatic agents. In particular, the compounds of Formula A are useful as immunosuppressive agents, particularly for treatment of allograft rejection, espeicically including cardiac allograft rejection, pancreatic allograft rejection and renal allograft rejection, and for treating autoimmune diabetest. These compounds can be used both prophylactically (e.g., in the methods of treatment for allograft rejection) and thereapeutically.

Testing

Initial animal screening tests to determine anti-inflammatory activity potential include the adjuvant arthritis assay according to the method of Pearson, *Proc. soc. Exp. Biol. Med.*, 91:95–101 (1956).

Also, in vitro tests, for example those using synovial explants from patients with rheumatoid arthritis, Dayer, et al., *J. Exp. Med.*, 145:1399–1404 (1977), are useful in determining whether compounds exhibit anti-inflammatory activity.

Autoimmune activity is determined utilizing experimental allergic encephalomyelitis by a modification of a procedure initially described by Grieg, et al., *J. Pharmacol. Exp. Ther.*, 173:85 (1970).

Activity to prevent the rejection of organ or tissue allografts in experimental animals is determined e.g., as described by Hao, et al., *J. Immunol.*, 139:4022–4026 (1987).

Immunosuppressive activity is determined by both in vivo and in vitro procesures. In vivo activity is determined utilizing a modification of the Herne hemolytic plaque assay, [Jerne, et al., "The agar plaque technique for recognizing antibody producing cells", *Cell–bound Antibodies*, Amos, B. and Kaprowski, H. editors (Wistar Institute Press, Philadelphia, PA) 1963, p. 109]. In vivo activity is determined by an adaptation of the procedure described by Greaves, et al. ["Activation of human T and B lymphocytes by polyclonal mitogens", *Nature*, 248, 698–701 (1974)].

Anti-viral activity is determined by the procedure described by Smee, et al. ["Anti-Herpesvirus Activity of the Acyclic Nucleoside 9-(1,3-Dihydroxy-2-Propoxymethyl)-Guanine", *Antimicrobial Agents and Chemotherapy*, 23 (5), 676–682 (1983)] or as described by Planterose ["Antiviral and cytotoxic effects of mycophenolic acid", *Journal of General Virology*, 4, 629 (1969)].

Tests for systemic activity in psoriasis can be carried out as described by Spatz, et al. ["Mycophenolic acid in psoriasis", *British Journal of Dermatology*, 98, 429 (1978)].

Tests for anti-tumor activity can be performed as described by Carter, et al. ["Mycophenolic acid: an anti-cancer compound with unusual properties", *Nature*, 223, 848 (1969)].

General Administration

Administration of the active compounds of Formula A, in pure form or in an appropriate pharmaceutical composition can be carried out via any of the accepted modes of administration of agents for serving similar utilities. Thus, administration can be, for example, orally, nasally, parenterally or topically, in the form of solid, semi-solid, lyophilized powder, or liquid dosage forms, such as for example, tablets, suppositories, pills, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an active compound of Formula A and, in addition, may include other medicinal agents, pharmaceutical agents, carriers, adjuvants, etc.

Generally, depending on the intended mode of administration, the pharamceutically acceptable compositions will contain about 1% to about 99% by weight of the pharmaceutically active compound of this invention and 99% to 1% by weight of suitable pharmaceutical excipients. Preferably, the composition will be about 5 to 75% by weight of a pharmaceutically active compound, with the rest being suitable pharmaceutical excipients.

The preferred manner of administration, for the conditions detailed above, is oral using a convenient daily dosage regimen which can be adjusted according to the degree of affliction. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, gum acacia, polyvinylpyrrolidone, gelatin, cellulose and derivatives thereof, and the like.

The active compounds of Formulas I may be formulated into a suppository using, for example, about 0.5% to about 50% active ingredient disposed in a carrier of polyethylene glycols (PEG) [e.g., PEG 1000 (96%) and PEG 4000 (4%)].

Liquid pharmaceutically administerable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see *Remington's Pharmaceutical Sciences*, 16th Ed., (Mach Publishing Company, Easton, PA, 1980). The composition to be administered will, in any event, contain a quantityof the active compound(s) in a pharmaceutically effective amount for relief of the particular condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.02 to 100 mg/kg of body weight per day of an active compound of Formula A. Most conditions respond to treatment comprising a dosage level on the order of 0.4 to 30 mg/kg of body weight per day, and most preferably about 10 mg/kg/day. Thus, for administration to a 70 kg person, the dosage range would be about 1.4 mg to 7 g per day, preferably about 7.0 to 700 mg per day.

EXAMPLES

The following examples are given to enable those skilled in the art to more clearly understand and to practice the present invention. They should not be considered as a limitation on the scope of the invention, but merely as being illustrative and representative thereof.

EXAMPLE 1

Morpholinoethyl E-6-(1,3-dihydro-4hydroxy-6-methoxy-7-methyl-3-oxo-5-isobenzofuranyl)-4-methyl-4hexenoate 1A. Formula A where Z is Hydrogen E-6-(1,3-dihydro-4-hydroxy-6-methoxy-7-methyl-3-oxo-5-isobenzofuranyl)-4-methyl-4-hexenoic acid (mycophenolic acid) (32.0 g) was dissolved in dichloromethane (250 ml), followed by the addition of thionyl chloride (25.0 ml) and dimethylformamide (0.3 ml). The reaction mixture was stirred at room temperature for 3 hours, after which the volatile components were removed under vacuum to afford E-6-(1,3-dihydro-4-hydroxy-6-methoxy-77-methyl-3oxo-5-isobenzofuranyl)-4-methyl-4-hexenoic acid chloride as an oil.

A solution of morpholinoethanol (30.5 ml) in dichloromethane (250 ml) was chilled to 4° C. on an ice bath. The mycophenolic acid chloride oil was dissolved in dichloromethane (50.0 ml) and added to the chilled solution. After stirring for 90 minutes (at 4° c.), the reaction mixture was washed with water and then with aqueous sodium bicarbonate. The organic solution was dried with sodium sulphate and evaporated to yield morpholinoethyl E-6-(1,3-dihydro-4-hydroxy-6-methoxy-7-methyl-3-oxo-5-isobenzofuranyl)-4-methyl-4-hexenoate (m.p. 93°–94° c.).

EXAMPLE 2

Morpholinoethyl E-6-(1,3-dihydro-4-acetoxy-6-methoxy-7-methyl-3-oxo-5-isobenzofuranyl)-4-methyl-4-hexenoate 2A. Formula A where Z is —C(O)CH$_3$ Morpholinoethyl E-6-(1,3-dihydro-4-hydroxy-6-methoxy-7-methyl-3-oco-5-isobenzofuranyl)-4-methyl-4-hexenoate (10.0 g) was dissolved in pyridine (50.0 ml) followed by the addition of acetic anhydride (10.0 ml). The mixture was stirred at room temperature for 90 minutes, then poured into water and extracted with ethyl acetate. The organic solution was dried and evaporated to give morpholinoethyl E-6-(1,3-dihydro-4-acetoxy-6-methoxy-7-methyl-3-oxo-5-isobenzofuranyl)-4-methyl-4-hexenoate.

2B. Formula A where Z is Other Than —C(O)CH$_3$

Similarly, by following the procedure of part A above and substituting for acetic anhydride the following materials:
propionyl chloride,
2-methylpropionyl chloride,
pivaloyl chloride, and
benzoyl bromide;
there are obtained the following respective compounds:
morpholinoethyl E-6-(1,3-dihydro-4-propionyloxy-6-methoxy-7-methyl-3-oxo-5-isobenzofuranyl)-4-methyl-4-hexenoate,
morpholinoethyl E-6(1,3-dihydro-4-(2-methyl-propionylosy)-6methoxyl-7-methyl-3-oxo-5-isobenzofuranyl]-4-methyl-4-hexenoate,
morpholinoethyl E-6-(1,3-dihydro-4-pivaloyloxy-6-methoxy-7-methyl-3-oxo-5-isobenzofuranyl)-4-methyl-4-hexenoate, and
morpholinoethyl E-6-(1,3-dihydro-4-benzoyloxy-6-methoxy-7-methyl-3oxo-5-isobenzofuranyl)-4methyl-4-hexenoate.

EXAMPLE 3

Morpholinoethyl E-6-(1,3-dihydro-4-hydroxy-6-methoxy-7methyl-3-oxo-5-isobenzofuranyl)-4-methyl-4-hexenoate hydrochloride 3A. Hydrochloride Salt of Formula A where Z is Hydrogen Morpholinoethyl E-6-(1,3-dihydro-4-hydroxy-6-methoxy-7-methyl-3-oxo-5-isobenzofuranyl)-4-methyl- 4-hexenoate (38.0 g) was dissolved in isopropanol (200 ml) and the solution was added to a solution of hydrogen chloride (10.0 g) in isopropanol (150 ml). The hydrochloride salt was collected by filtration and dried under vacuum (m.p. 154°–155° C.).

3B. Hydrochloride Salts of Formula A where Z is Other Than —C(O)CH₃

Similarly, by following the procedure of part A above and substituting for morpholinoethyl E-6--(1,3-dihydro-4-hydroxy-6-methoxy-7-methyl-3-oxo-5-isobenzofuranyl)-4-methyl-4-hexenoate the following materials (prepared, e.g., as in Example 2B):
morpholinoethyl E-6-(1,3-dihydro-4-propionyloxy-6-methoxy-7-methyl-3-oxo-5-isobenzofuranyl)-4-methyl-4hexenoate,
morpholinoethyl E-6-(1,3-dihydro-4-(2-methylpropionyloxy)-6methoxy-7methyl-3-oxo-5-isobenzofuranyl]-4-methyl-4-hexenoate,
morpholinoethyl E-6-(1,3-dihydro-4-pivaloyloxy-6-methoxy-7-methyl-3-oxo-5-isobenzofuranyl)-4methyl-4-hexenoate, and
morpholinoethyl E-6-(1,3-dihydro-4-benzoyloxy-6l-methoxy-7-methyl-3-oxo-5-isobenzofuranyl)-4-methyl-4-hexenoate;
there are obtained the following respective compounds:
morpholinoethyl E-6-(1,3-dihydro-4-propionyloxy-6-methoxy-7-methyl-3-oxo-5-isobenzofuranyl)-4-methyl-4-hexenoate hydrochloride (m.p. 140°–144° C.),
morpholinoethyl E-6-[1,3-dihydro-4-(2-methylpropionyloxy)-6-methoxy-7-methyl-3oxo-5isobenzofuranyl]-4-methyl-4hexenoate hydrochloride,
morpholinoethyl E-6-(1,3-dihydro-4l-pivaloyloxy-6-methoxy-7-methyl-3oxo5isobenzofuranyl)-4-methyl-4hexenoate hydrochloride (m.p. 135°–139° C.), and
morpholinoethyl E-6-(1,3-dihydro-4-benzoyloxy-6-methoxy-7-methyl-3-oxo-5-isobenzofuranyl)-4-methyl-4-hexenoate hydrochloride.

EXAMPLE 4

Morpholinoethyl E-6-(1,3-dihydro-4-hydroxy-6-methoxy-7-methyl-3-oxo-5-isobenzofuranyl)-4-methyl-4-hexenoate bisulfate 4a. Bisulfate Salt of Formula A where Z is Hydrogen Morpholinoethyl E-6-(1,3-dihydro-4-hydroxy-6-methoxy-7-methyl-3l-oxo-5-isobenzofuranyl)-4-methyl-4-hexenoate (4.6 g) was dissolved in ethyl acetate (50 ml) and the solution was added to a solution of sulfuric acid (1.25 g) in isopropanol (50 ml). The bisulfate salt was collected by filtration, washed with ethyl acetate and dried under vacuum at 50° C. (m.p. 143°–145° C.).

4B. Bisulfate Salts of Formula A where Z is Other Than —C(O)CH₃

Similarly, by following the procedure of part A above and substituting for morpholinoethyl E-6-(1,3-dihydro-4-hydroxy-6-methoxy-7-methyl-3-oxo-5-isobenzofuranyl)-4-methyl-4-hexenoate the materials prepared in Example 2B, the corresponding bisulfate salts are obtained.

EXAMPLE 5

This example illustrates the preparation of a representative pharmaceutical formulation for oral administration containing an active compound of Formula A, e.g., morpholinoethyl E-6-(1,3-dihydro-4-hydroxy-6-methoxy-7-methyl-3oxo-5-isobenzofuranyl)-4methyl-4hexenoate hydrochloride.

| Ingredients | Quantity per tablet, mgs. |
|---|---|
| Active compound | 200 |
| lactose, spray-dried | 148 |
| magnesium stearate | 2 |

The above ingredients are mixed and introduced into a hard-shell gelatin capsule.

Other compounds of Formula A, such as those prepared in accordance with Examples 2–4, can be used as the active compound in the preparation of the orally administrable formulations of this example.

EXAMPLE 6

This example illustrates the preparation of another representative pharmaceutical formulation for oral administration, containing an active compound of Formula A, e.g., morpholinoethyl E-6-(1,3-dihydro-4-hydroxy-6-methoxy-7-methyl-3-oxo-5-isobenzofuranyl)-4-methyl-4-hexenoate hydrochloride.

| Ingredients | Quantity per tablet, mgs. |
|---|---|
| Active compound | 400 |
| cornstarch | 50 |
| lactose | 145 |
| magnesium stearate | 5 |

The above ingredients are mixed intimately and pressed into single scored tablets.

Other compounds of Formula A, such as those prepared in accordance with Examples 2–4, can be used as the active compound in the preparation of the orally administrable formulations of this example.

EXAMPLE 7

This example illustrates the preparation of a representative pharmaceutical formulation containing an active compound of Formula A, e.g., morpholinoethyl E-6-(1,3-dihydro-4-hydroxy-6-methoxy-7-methyl-3-oxo-5-isobenzofuranyl)-4methyl-4-hexenoate hydrochloride.

An oral suspension is prepared having the following composition:

| Ingredients | |
|---|---|
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Other compounds of Formula A, such as those prepared in accordance with Examples 2–4, can be used as the active compound in the preparation of the orally administrable formulations of this example.

EXAMPLE 8

This example illustrates the preparation of a representative pharmaceutical formulation containing an active compound of Formula A, e.g., morpholinoethyl E-6-(1,3-dihydro-4-hydroxy-6-methoxy-7-methyl-3-oxo-5-isobenzofuranyl)-4-methyl-4-hexenoate hydrochloride.

An injectable preparation buffered to a pH of 4 is prepared having the following composition:

| Ingredients | |
|---|---|
| Active compound | 0.2 g |
| Sodium Acetate Buffer Solution (0.4M) | 2.0 ml |
| HCl (1N) | q.s. to pH 4 |
| water (distilled, sterile) | q.s. to 20 ml |

Other compounds of Formula A, such as those prepared in accordance with Examples 2–4, can be used as the active compound in the preparation of the injectable formulations of this example.

EXAMPLE 9

This example illustrates the preparation of a representative pharmaceutical formulation for topical application containing an active compound of Formula A, e.g., morpholinoethyl E-6-(1,3-dihydro-4-hydroxy-6-methoxy-7-methyl-3-oxo-5-isobenzofuranyl)-4-methyl-4-hexenoate hydrochloride.

| Ingredients | grams |
|---|---|
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula A, such as those prepared in accordance with Examples 2–4, can be used as the active compound in the preparation of the topical formulations of this example.

EXAMPLE 10

This example illustrates the preparation of a representative pharmaceutical formulation containing an active compound of Formula A, e.g., morpholinoethyl E-6-(1,3dihydro-4-hydroxy-6-methoxy-7methyl-3oxo-5-isobenzofuranyl)-4-methyl-4-hexenoate hydrochloride.

A suppository totally 2.5 grams is prepared having the following composition:
Active compound: 500 mg
witepsol H-15*: balance
(*triglycerides of saturated vegetable fatty acid; a product of Riches-Nelson, Inc., New York, N.Y.).

Other compounds of Formula A, such as those prepared in accordance with Examples 2–4, can be used as the active compound in the preparation of the suppository formulations of this example.

EXAMPLE 11

Determination of Anti-Inflammatory Activity Utilizing Adjuvant-Induced Arthritis In the Rat Protocol:

This procesure is a modification of a procedure initially described in Pearson, C. M., *Proc. Soc. Exp. Boil. Med.*, 91:95–101 (1956).

Female Simonsen albino rats weighing 160–180 g receive 0.1 ml of a suspension in paraffin oil of heat-killed M. *Mycobacterium butyricum* (10 mg/ml) by means of an intradermal injection into the proximal ¼ of the tail on day 0. Beginning on day 1, the test material is administered orally in an aqueous vehicle (0.5 ml/dose) twice each day for 17 days. On day 18 the intensity of the swelling of the four foot pads and tail is determined utilizing a scoring system in which the swelling in the four paws was scored 0–4 for each paw and the tail swelling is scored 0–3, such that the total maximum score is 19.

The compounds of the present invention show anti-inflammatory activity when tested by this method.

EXAMPLE 12

Determination of Autoimmune Activity Utilizing Experimental Allergic Encephalomyelitis Protocol:

This procedure is a modification of a procedure initiall described by Grieg, et al., *J. Pharmacol. Exp. Ther.* 173:85 (1970).

On day 1, Experimental Allergic Encephalomyelitis is induced by giving an 0.1 ml sub-planter injection into the dorsum of the right hind paw of an emulsion consisting of 15 mg (wet weight) of syngenic spinal cord tissue, 0.06 ml of Freund's Incomplete Adjuvant (Difco), 0.04 ml of sterile 0.9% saline, and 0.2 mg of heat killed and dried Mycobacterium butyricum (Difco). On days 12–17, clinical evaluations are obtained for each animal. The animals are considered positive if flaccid hind limb paralysis is present on one or more days.

The compounds of the present invention show autoimmune activity when tested by this method.

EXAMPLE 13

Determination of Immunosuppressive Activity Utilizing The Hemolytic Plaque Forming Cell Assay This procedure is a modification of "The agar plaque technique for recognizing antibody producing cells", a procedure initially described by Jerne, et al. [*Cellbound Antibodies*, Amos and Kaprowski editors (Wistar Institute Press, Philadelphia, 1963) p. 109].

Groups of 5–6 adult C578B1/6 male mice were sensitized with $1 \times 10^8$ sheep red blood cells ("SRBC") and simultaneously treated with an oral dosage form of the test material in an aqueous vehicle. Animals in a control group receive the same volume of vehicle. Four days after SRBC inoculation, spleens are dispersed in loose Ten Broeck homogenizers. The number of nucleated cells ("WBC") is determined and the spleen cell suspension is mixed with SRBC, guinea pig complement and agar solution at 0.5% concentration. Aliquots of the above mixture (0.1 ml) are dropped on four separate quadrants of a Petri dish and are covered with cover slips. After two hours incubation at 37° C., areas of hemolysis around plaque-forming cells ("PFC") are counted with a dissecting microscope. Total WBC/spleen, PFC/spleen and $PFC/10^6$ WBC ("PPM") are calculated for each mouse spleen. Geometric means of each treatment group are then compared with the vehicle-treated control group.

The compounds of the present invention show immunosuppressive activity when tested by this method.

EXAMPLE 14

Determination of Immunosuppressive Activity Utilizing Responses of Human Peripheral Blood Lymphocytes to T- and B-cell Mitogens This procedure is a modification of a procedure initially described by Greaves, et al. ["Activation of human T and B lumphocytes by polyclonal mitogens", *Nature*, 248, 698–701 (1974)].

Human mononuclear cells ("PBL") are separated from heparinized whole blood by density gradient centrifugation in Ficoll-Paque (Pharmacia). After washing, $2 \times 10^5$ cells/well are cultured in microtiter plates with RPMI 1640 supplemented with 5% fetal calf serum, penicillin and streptomycin. To evaluate differential effects on T- and B-lymphocytes, different mitogens are used: PHA (Sigma) at 10 μg/ml, PWM (Sigma) at 20 μg/ml and Staphylococcus Protein A bound to Sepharose (SPA) (Sigma) 2 mg/ml or 14 μg/ml of Protein A. Test materials are tested at concentrations between $10^4$ and $10^8$ M, by addition to the culture at time 0. Cultures are set up in quadruplicate and incubated at 37° C. in a humidified atmosphere with 7% $CO_2$ for 72 hours. A pulse of 0.5 μCi/well of $^3$H-thymidine is added for the last 6 hours. Cells are collected on glass fiber filters with an automatic harvester and radioactivity is measured by standard scintillation procedures. the 50% inhibitory concentration ("$IC_{50}$") for mitogenic stimulation is determined graphically.

The compounds of the present invention show immunosuppressive activity when tested by this method.

EXAMPLE 15

Determination of Anti-viral Activity Utilizing 50% Plaque Reduction Assay

This procedure is described by Smee, et al., in "Anti-Herpesvirus Activity of the Acyclic Nucleeoside 9-(1,3-Dihydroxy-2-Propoxymethyl)Guanine" [*Antimicrobial Agents and Chemotherapy*, 23(5), 676–682 (1983)].

Confluent monolayers of Vero cells in six-well Costar microplates (Bellco Glass, Inc., Vineland, N.J.) are infected with 100 to 200 PFU of HSV or pseudorabies virus. After a 1.25 hour adsorption period, the virus is aspirated and EMEM containing 0.6% methylcellulose, 2% fetal bovine serum, 0.25% $NaHCO_3$, 10 mM HEPES buffer, 50 μg of gentamicin per ml, and the test compopund are applied. Three wells per dilution of the test compound, and six control wells without test compound are incubated for four days at 37° C. in 5% $CO_2$, after which the methylcellulose layer is removed and the cells are fixed with methanol for 10 minutes and stained with 10% Giemsa stain (Fisher Scientific co., Fair Lawn, N.J.) for 20 minutes. After the plates are aspirated and dried, the plaques are counted at 13X magnification with a Bellco plaque viewer. Drug concentrations that reduced plaque numbers by 50% [the 50% inhibitory does ($ID_{50}$)] are calculated, e.g., with a computer using a semilog probit analysis program [see Finney, D. J., *Probit analysis*, 3rd Ed., p. 333, (Cambridge University Press, London, 1971)].

The compounds of the present invention show antiviral activity when tested by this method.

EXAMPLE 16

Bioavailability —Plasma Levels

Compounds of Formula a are given to four male cynomolgus monkeys as a solid dosage form (about 20 mg/kg body weight) with one-week intervals between doses. Mtycophenolic acid is given to a control group. The compounds are weighed into hard gelatin capsules and administered orally. Samples of plasma are obtained at 0.25, 0.5, 1, 3, 5, 7 and 24 hours after dosing, and are analyzed for concentrations of mycophenolic acid by HPLC.

Compounds of the present invention where Y is morpholinoethyl, [morpholinoethyl E-6-(1,3-dihydro-4hydroxy-6methoxy-7-methyl-3oxo-5-isobenzofuranyl)-4methyl-4hexenoate hydrochloride and morpholinoethyl E-6-(1,3-dihydro-4-acetoxy-6-methoxy-7-methyl-3-oxo-5isobenzofuranyl)-4-methyl-4-hexenoate hydrochloride] were compared to mycophenolic acid according to the above protocol. The compounds of the present invention where Y is morpholinoethyl demonstrated faster absorption to higher peak plasma levels than mycophenolic acid.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, proces step or steps, to the objective, spirit and scope of the present invention. All such modifications are intended to be within the scope of the claims appended hereto.

What is claimed is:

1. A method of treating autoimmune diseases, which comprises administering to a mammal in need thereof a therapeutically effective amount of a compound represented by the formula:

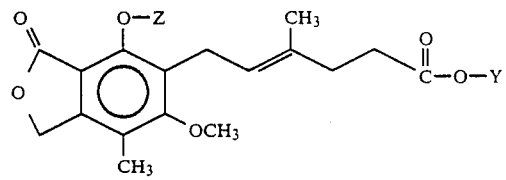

wherein:
Y is hydrogen; and
Z is hydrogen or —C(O)R,
where R is lower alkyl or aryl;
or a pharmaceutically acceptable salt thereof.

2. The method of claim 1 comprising a method of treating autoimmune diabetes.

3. The method of claim 2 wherein Z is hydrogen.

4. The method of claim 1 wherein Z is hydrogen.

5. A pharmaceutical formulation comprising a compound represented by the formula:

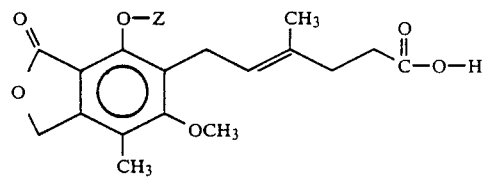

wherein Z is hydrogen or —C(O)R where R is lower alkyl or aryl, or a pharmaceutically acceptable salt thereof, in an amount sufficient to administer from about 0.4 mg/kg to 30 mg/kg per day of said compound to a mammal in need thereof,
and a pharmaceutically acceptable carrier suitable for injection.

6. The pharmaceutical formulation of claim 5 wherein Z is hydrogen.

* * * * *